US006483302B1

(12) United States Patent
Rusnell et al.

(10) Patent No.: US 6,483,302 B1
(45) Date of Patent: Nov. 19, 2002

(54) METHOD AND APPARATUS FOR MAGNETIC INSPECTION OF FERROUS CONDUIT FOR WEAR

(75) Inventors: David Grant Rusnell, Edmonton (CA); Timothy Dayn Rogers, Sherwood Park (CA); William John Woods, Edmonton (CA); Ian Thomas Moss, Sherwood Park (CA)

(73) Assignee: R.D. Tech Inc., Bonnyville (CA)

( * ) Notice: Subject to any disclaimer, the term of this patent is extended or adjusted under 35 U.S.C. 154(b) by 103 days.

(21) Appl. No.: 09/615,695

(22) Filed: Jul. 7, 2000

(51) Int. Cl.[7] ............................ G01R 33/12; G01N 27/82
(52) U.S. Cl. ........................ 324/232; 324/235; 324/242
(58) Field of Search ................................ 324/220, 221, 324/228, 239, 240, 262, 227, 232, 242, 235

(56) References Cited

U.S. PATENT DOCUMENTS

| 4,555,665 A | 11/1985 | Stanley et al. | 324/229 |
| 4,710,712 A | 12/1987 | Bradfield et al. | 324/227 |
| 4,792,756 A | 12/1988 | Lam et al. | 324/232 |
| 5,030,911 A | 7/1991 | Lam | 324/226 |
| 5,377,553 A | 1/1995 | Knepper, Jr. | 73/866.5 |
| 5,671,155 A | 9/1997 | Edens et al. | 364/507 |
| 5,943,632 A | 8/1999 | Edens et al. | 702/38 |
| 5,963,030 A | 10/1999 | Stark | 324/229 |

FOREIGN PATENT DOCUMENTS

| CA | 1222287 | 5/1987 | 324/50 |
| CA | 1224249 | 7/1987 | 324/53 |

*Primary Examiner*—Edward Lefkowitz
*Assistant Examiner*—Reena Aurora
(74) *Attorney, Agent, or Firm*—Christensen O'Connor Johnson Kindness PLLC

(57) ABSTRACT

An apparatus for the magnetic inspection of ferrous conduit for signs of wear includes a housing having a first end, a second end and a conduit travel passage extending through the housing from the first end to the second end. At least one coil is positioned within the housing encircling the conduit travel passage. The coil is disposed at an angle to the conduit travel passage so as to create a transverse flux component. Sensor supports are positioned along the conduit travel passage encircled by the coil. At least one sensor array is mounted on the sensor supports. The sensor array is oriented to detect flux patterns which extend transversely relative to the conduit travel passage. A computer is in communication with the sensor array to receive and interpret signals from the sensor array.

19 Claims, 15 Drawing Sheets

METHOD AND APPARATUS FOR MAGNETIC INSPECTION OF FERROUS CONDUIT FOR WEAR

FIELD OF THE INVENTION

The present invention relates to a method and an apparatus for the magnetic inspection of ferrous conduit for signs of wear.

BACKGROUND OF THE INVENTION

Ferrous conduit, in the form of sections of pipe or continuous coil tubing, is used in numerous applications. For example, in an oil well, ferrous conduit extends from surface to the bottom of the well. Oil is lifted from the bottom of the well to surface by a screw pump, pump jack or other method. The screw pump is positioned at the bottom of the oil well and is turned by a drive unit positioned at the surface. The screw pump is connected to the drive unit by either sucker rods or co-rod that run the entire length of the conduit. The drivels unit rotates the sucker rods or co-rod to transfer torque to the screw pump.

When a screw pump has been operating for a period of time, wear patterns begin to develop on the conduit. The wear patterns experienced depend upon whether the rods connecting the screw pump and the drive unit are sucker rods or co-rods. Sucker rods come in finite lengths, usually 25 foot lengths. There are, therefore, joints every 25 feet where sucker rods are screwed together in end to end relation. As the sucker rod string rotates, the joints tend to wear a circumferential groove within the conduit. Co-rod continuous rod that runs the entire length of the conduit. As the co-rod rotates it tends to wear a longitudinal groove within the conduit.

If the conduit contains a flaw, such as a crack or a loss of metallic area, the conduit is susceptible to rupturing. As part of a program of preventative maintenance, the conduit is periodically inspected. Magnetic inspection apparatus have been developed for use in such preventative maintenance programs. An example of such a magnetic inspection apparatus is U.S. Pat. No. 5,671,155. This magnetic inspection apparatus induces magnetic fields in ferrous conduit. The changes in the induced magnetic field are then measured and signals are produced representative of those changes which are used to identify irregularities. The apparatus constructed in accordance with the teachings of the invention have, to date, only been suited for reliably detecting circumferential wear patterns. Such apparatus is not suited for reliably detecting longitudinal wear patterns.

SUMMARY OF THE INVENTION

What is required is a method and an apparatus for the magnetic inspection of ferrous conduit for signs of wear, that is capable of reliably detecting longitudinal wear patterns.

According to one aspect of the present invention there is provided an apparatus for the magnetic inspection of ferrous conduit for signs of wear which includes a housing having a first end, a second end and a conduit travel passage extending through the housing from the first end to the second end. At least one coil is positioned within the housing encircling the conduit travel passage. The coil is disposed at an angle to the conduit travel passage so as to create a transverse flux component. Sensor supports are positioned along the conduit travel passage encircled by the coil. At least one sensor array is mounted on the sensor supports. The sensor array is oriented to detect flux patterns which extend transversely relative to the conduit travel passage. A computer is in communication with the sensor array to receive and interpret signals from the sensor array.

The apparatus, as described above, is capable of detecting longitudinal wear patterns. It accomplishes such detection by using an angular oriented coil to create a transverse flux component and an array of sensors oriented to detect the transverse flux component. In order to avoid the necessity of multiple passes of conduit through the apparatus, it is preferred that the sensor supports and the sensor array be positioned to provide flux pattern detection over 360 degrees of the circumference.

Although beneficial results may be obtained through the use of the apparatus, as described above, it is preferred that two or more coils be used. Each of the two or more coils are disposed at a different angle in relation to the conduit travel passage. Sensor supports are positioned within each of the two or more coils. A sensor array is mounted on each of the sensor supports. With multiple coils, the coverage of the conduit is improved. One preferred configuration includes a first coil positioned within the housing encircling the conduit travel passage at a first angle and a second coil positioned within the housing encircling the conduit travel passage at a second angle. A first pair of sensor supports is positioned in parallel spaced relation on opposed sides of the conduit travel passage within the first coil. A second pair of sensor supports is positioned in parallel spaced relation on opposed sides of the conduit travel passage within the second coil. The second pair of sensor supports is offset by 90 degrees from the first pair of sensor supports.

Although beneficial results may be obtained through the use of the apparatus, as described above, in most applications it is desirable to inspect the conduit for both longitudinal wear patterns and circumferential wear patterns. Even more beneficial results may, therefore, be obtained when each sensor support includes a first sensor array and a second sensor array. The first sensor array is oriented to detect flux patterns which extend transversely relative to the conduit travel passage. The second sensor array is oriented to detect flux patterns which extend longitudinally relative to the conduit travel passage.

Although beneficial results may be obtained through the use of the apparatus, as described above, it is desirable to get the sensors as close as possible to the conduit in order to improve the sensitivity to a level where small defects or degree of wear can be detected. Even more beneficial results may, therefore, be obtained when the sensor supports are concave and are oriented to conform to the contour of conduit passing through the conduit travel passage.

Although beneficial results may be obtained through the i use of the apparatus, as described above, with a string of joined conduits joints are encountered at periodic intervals. Even more beneficial results may, therefore, be obtained when the sensor supports are mounted on springs. The springs enable the spacing between the sensor supports to adjust when passing over joints in conduit. This movement over joints can be enhanced by the addition of some further features. Even more beneficial results may be obtained when the sensor supports are mounted for limited pivotal movement about a centrally positioned transverse axis. Even more beneficial results may be obtained when the sensor supports have a wedge shaped inclined interior contact surface on at least one end.

Although beneficial results may be obtained through the use of the apparatus, as described above, it is important for sensor accuracy that the conduit always is properly aligned within the conduit travel passage. Even more beneficial results may be obtained when guide rollers are mounted to the housing surrounding the conduit travel passage to center housing around conduit passing through the conduit travel passage.

Although beneficial results may be obtained through the use of the apparatus, as described above, when conduit is pulled from an oil well during a field inspection, it is covered in oil. Even more beneficial results may, therefore, be obtained when a resilient annular wiper encircles the conduit travel passage and engages conduit prior to passing through the conduit travel passage to remove excess oil.

According to another aspect of the present invention there is provided a method for the magnetic inspection of ferrous conduit for signs of wear. A first step involves positioning a coil encircling a conduit travel path at an angle so as to create a transverse flux component. A second step involves positioning a sensor array along the conduit travel path encircled by the at least one coil, with the sensor array oriented to detect flux patterns which extend transversely relative to the conduit travel passage. A third step involves using a computer in communication with the sensor array to receive and interpret signals from the sensor array.

Although beneficial results may be obtained through the use of the method, as described above, it has been determined that the sensitivity of the apparatus to small imperfections can be enhanced when the amperage in the coil is kept constant.

Although beneficial results may be obtained through the use of the method, as described above, it has been determined that the large volume of data generated can best be handled when analog signals from the sensor are immediately converted to digital signals at their source prior to communication to the computer.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
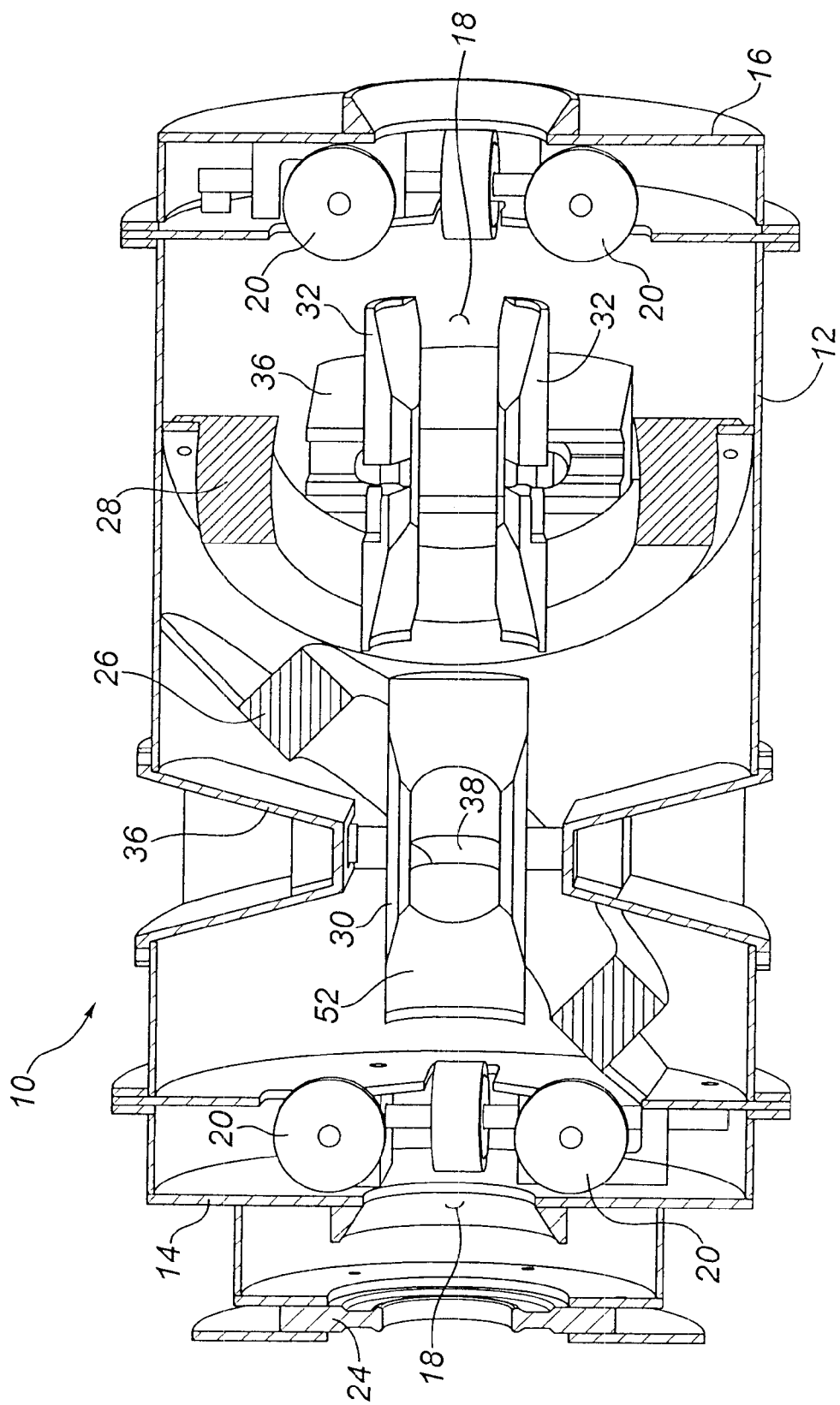
FIG. 1 is a front elevation view, in section, of an apparatus for the magnetic inspection of ferrous conduit for signs of wear constructed in accordance with the teachings of the present invention.

The preferred embodiment, an apparatus for the magnetic inspection of ferrous conduit for signs of wear generally identified by reference numeral 10, will now be described with reference to FIGS. 1 through 17.

Structure and Relationship of Parts:

Referring to FIG. 1, apparatus 10 includes a housing 12 that has a first end 14, a second end 16 and a conduit travel passage 18 extending through housing 12 from first end 14 to second end 16. 4

Referring to FIGS. 1, 2, 4 and 5, the illustrated. embodiment has four spring biased guide rollers 20 mounted to housing 12 surrounding conduit travel passage 18 to center housing 12 around conduit 22 as conduit 22 passes into and through conduit travel passage 18. Referring to FIG. 1, a resilient annular wiper 24 encircles conduit travel passage 18 and engages conduit 22 passing through conduit travel passage 18 to remove excess oil.

Figure 3:
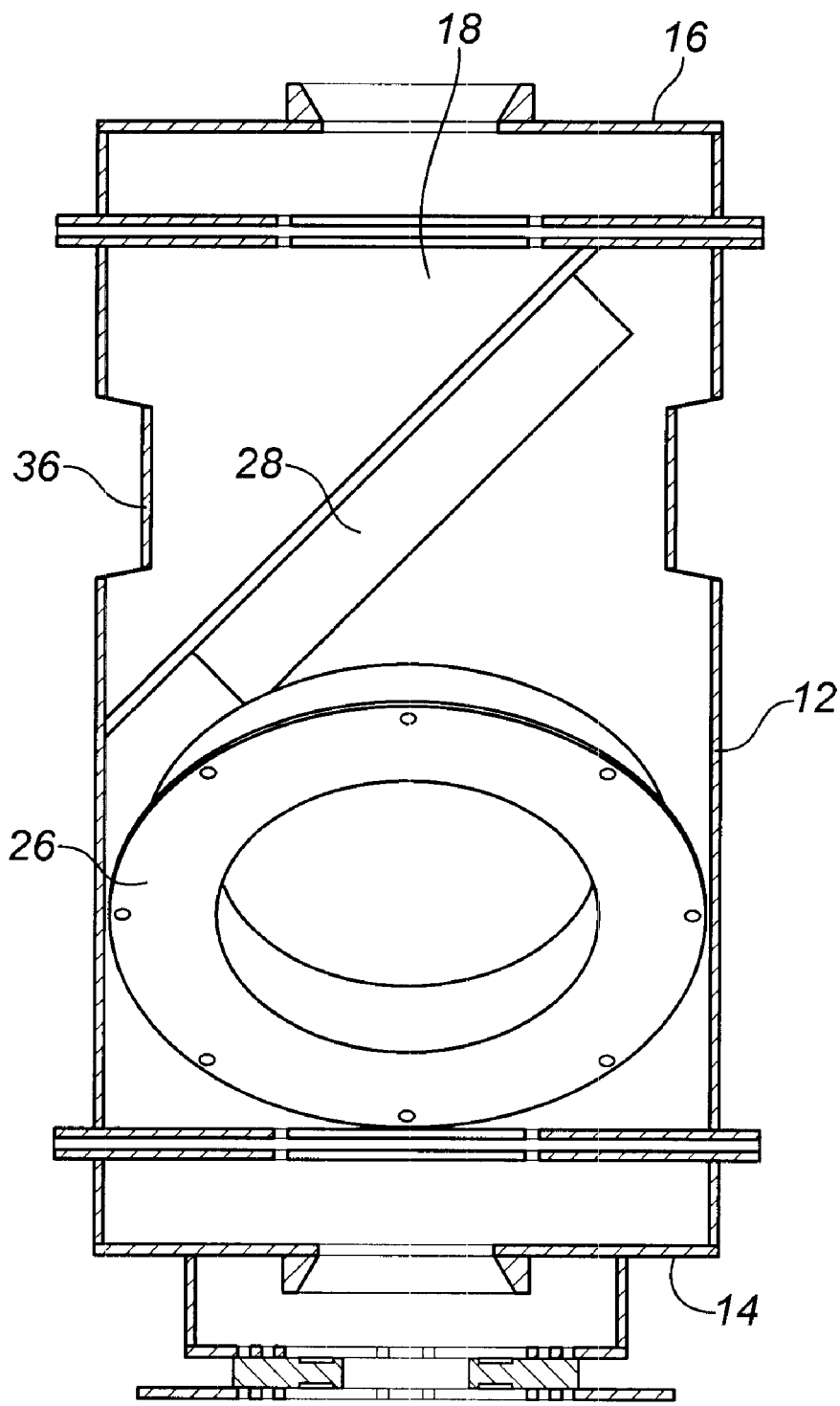
FIG. 3 is a side elevation view, in section, of the apparatus illustrated in FIG. 1.

Referring to FIGS. 1 and 3, a first coil 26 is positioned within housing 12 encircling conduit travel passage 18. First coil 26 is disposed at a first angle of approximately 45 degrees to conduit travel passage 18 so as to create a transverse flux component. A second coil 28 is positioned within housing 12 encircling conduit travel passage 18. Second coil 28 is disposed at a second angle of approximately 45 degrees to conduit travel passage 18 so as to create a transverse flux component perpendicular to that produced by first coil 26.

Figure 9:
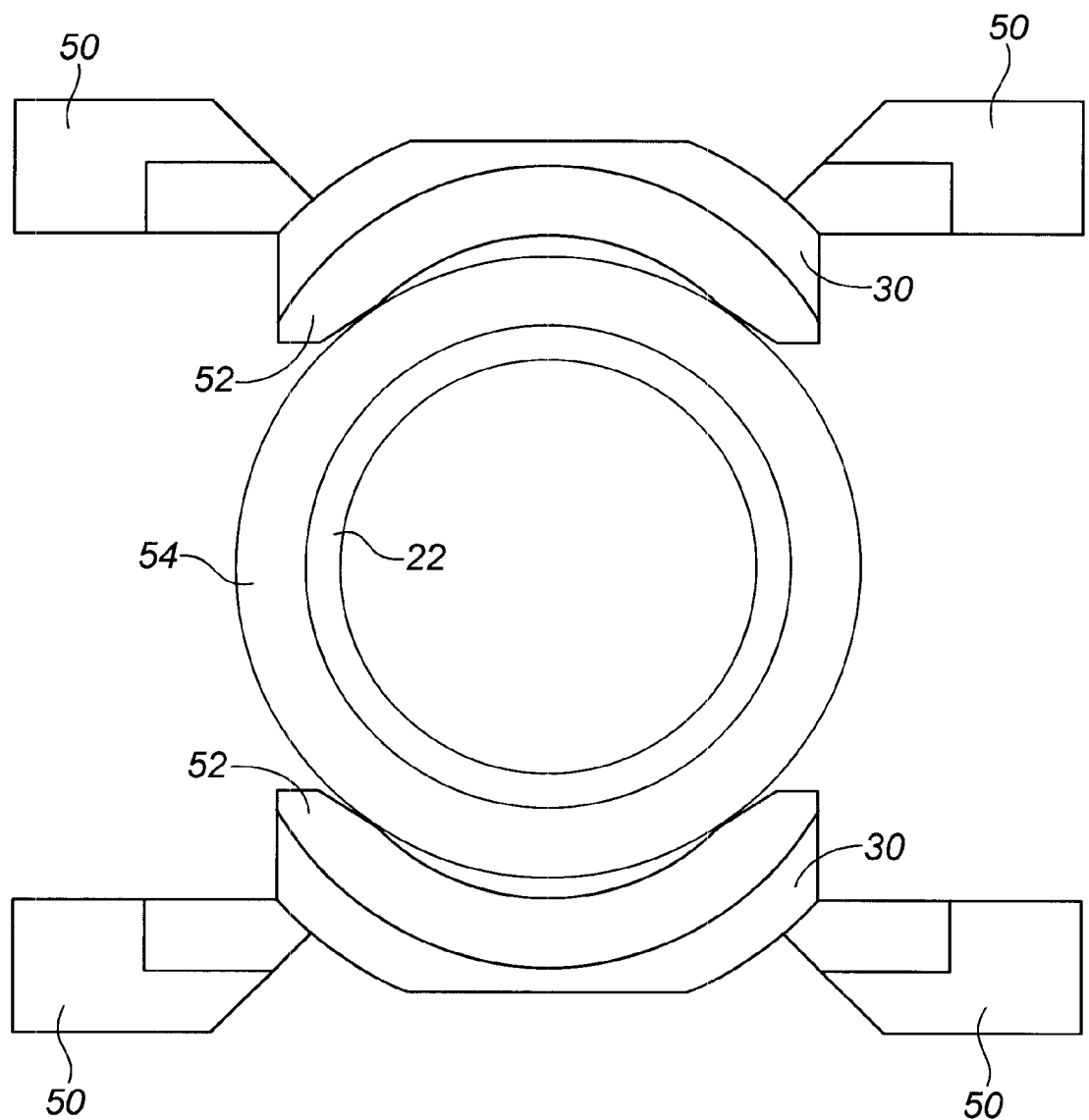
FIG. 9 is an end elevation view of the sensor supports as a joint passes through the conduit travel passage of the apparatus illustrated in FIG. 1.
Figure 10:
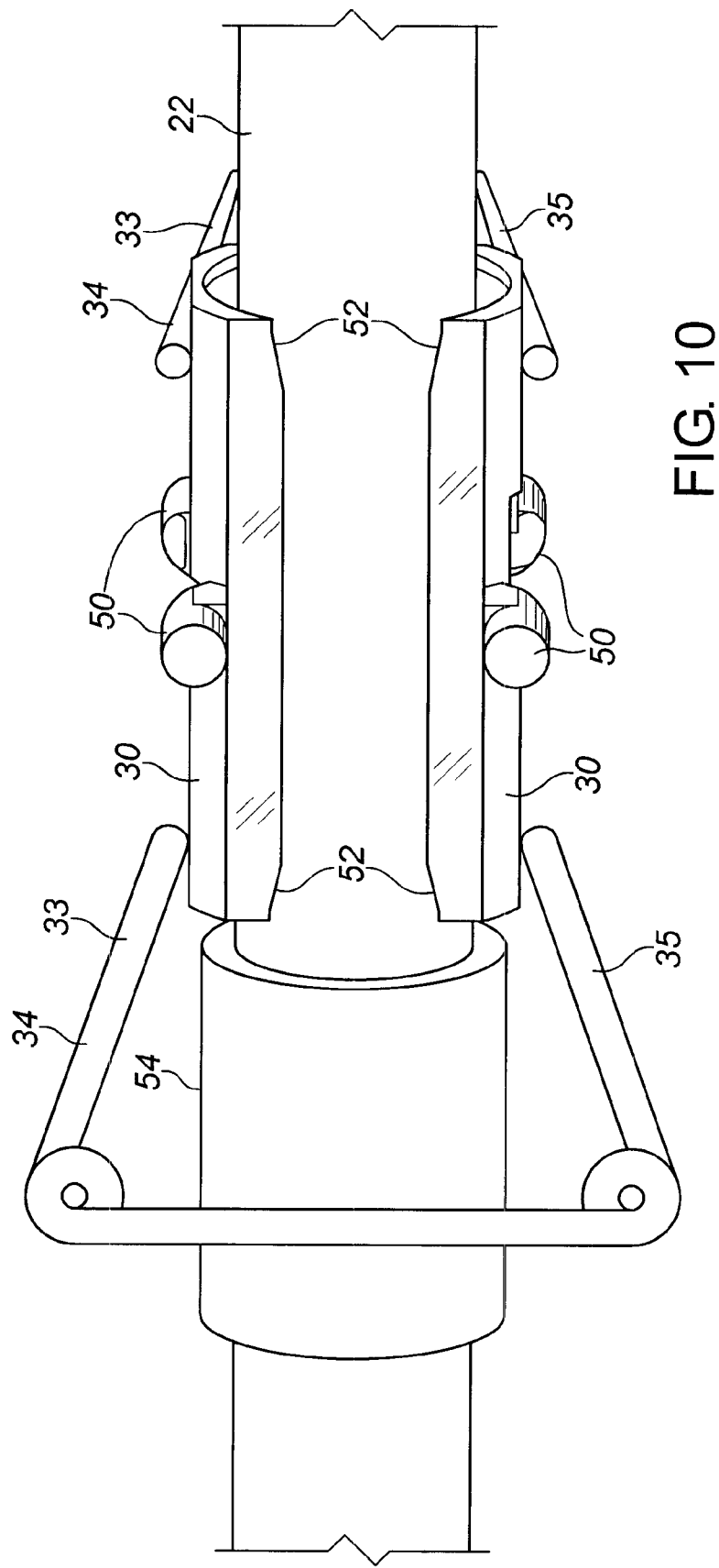
FIG. 10 is a side elevation view of the sensor supports as a conduit passes through the conduit travel passage of the apparatus illustrated in FIG. 9.

Referring to FIG. 1, a first pair of sensor supports 30 are positioned in parallel spaced relation on opposed sides of conduit travel passage 18 within first coil 26. First pair of sensor supports 30 are concave and oriented to conform to the contour of conduit 22 passing through conduit travel passage 18 as illustrated in FIGS. 9 and 10.

A second pair of sensor supports 32 are positioned in parallel spaced relation on opposed sides of conduit travel passage 18 within second coil 28. Second pair of sensor supports 32 are offset by 90 degrees from first pair of sensor supports 30. Second pair of sensor supports 32 are also concave and oriented to conform to the contour of conduit 22 passing through conduit travel passage 18.

Figure 6:
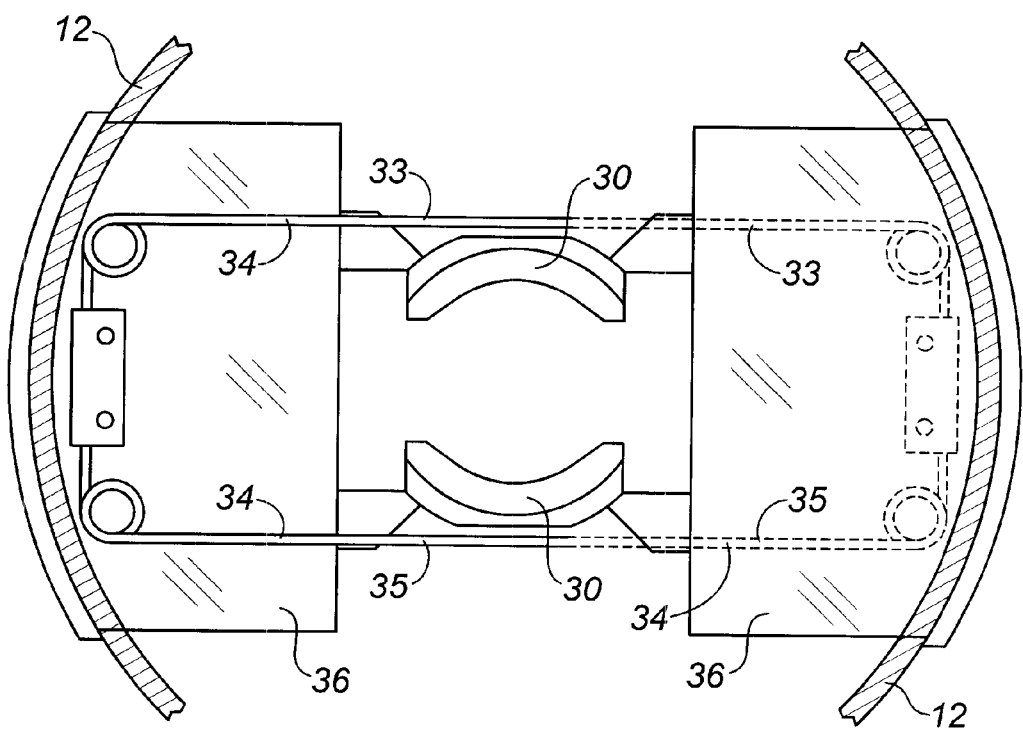
FIG. 6 is a detailed top plan view of a spring mounting for the sensor supports from the apparatus illustrated in FIG. 1.

Referring to FIGS. 1 and 6, each of first pair of sensor supports 30 and second pair of sensor supports 32 are positioned by a pair of springs 34 positioned opposite to each other. Springs 34 are supported in underlying relation by sensor support mounts 36 which project inwardly from housing 12. As illustrated in FIGS. 6 and 10, a first arm 33 of each of pair of springs 34 engages with one of first pair of sensor supports 30 while a second arm 35 engages with the other of first pair of sensor supports 34.

Figure 7:
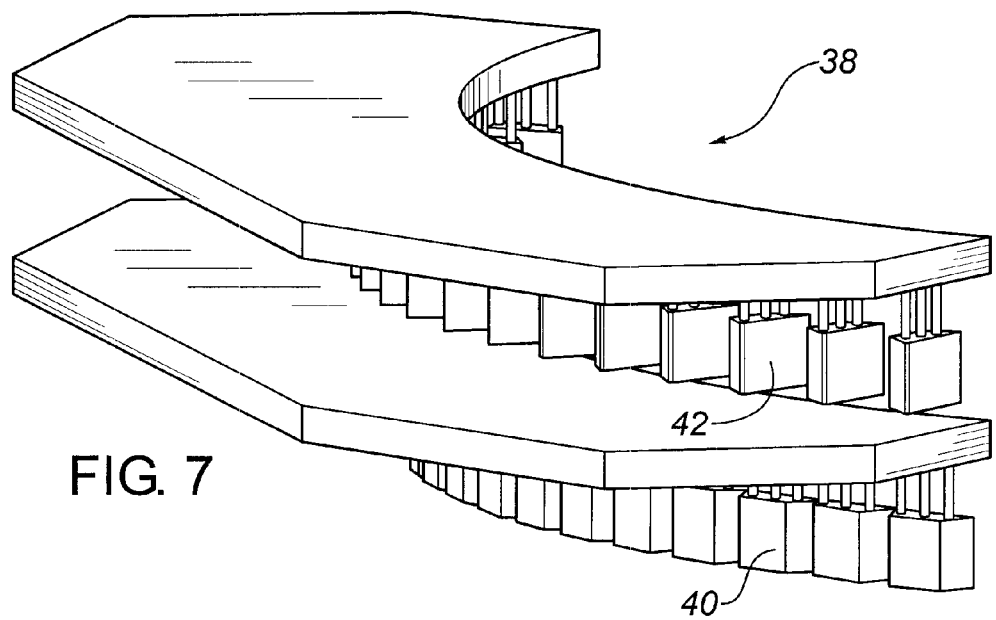
FIG. 7 is a detailed perspective view of sensor arrays.
Figure 8:
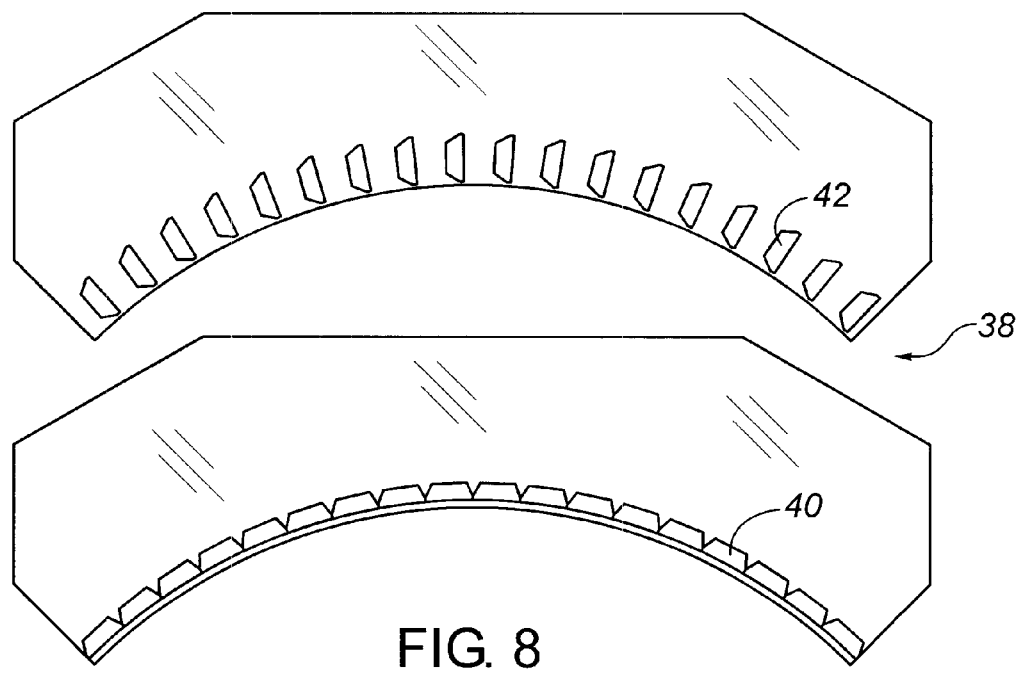
FIG. 8 is an exploded view of the sensor arrays from the apparatus illustrated in FIG. 7.

Referring to FIGS. 1, 7 and 8, sensor arrays, generally indicated by reference numeral 38, are mounted on each of first pair of sensor supports 30 and each of second pair of sensor supports 32 in an arcuate pattern.

Referring to FIG. 7, sensor arrays 38 include a first sensor array 40 oriented to detect flux patterns which extend radially relative to conduit travel passage 18, and a second sensor array 42 oriented to detect flux patterns which extend transversely relative to conduit travel passage 18.

Figure 4:
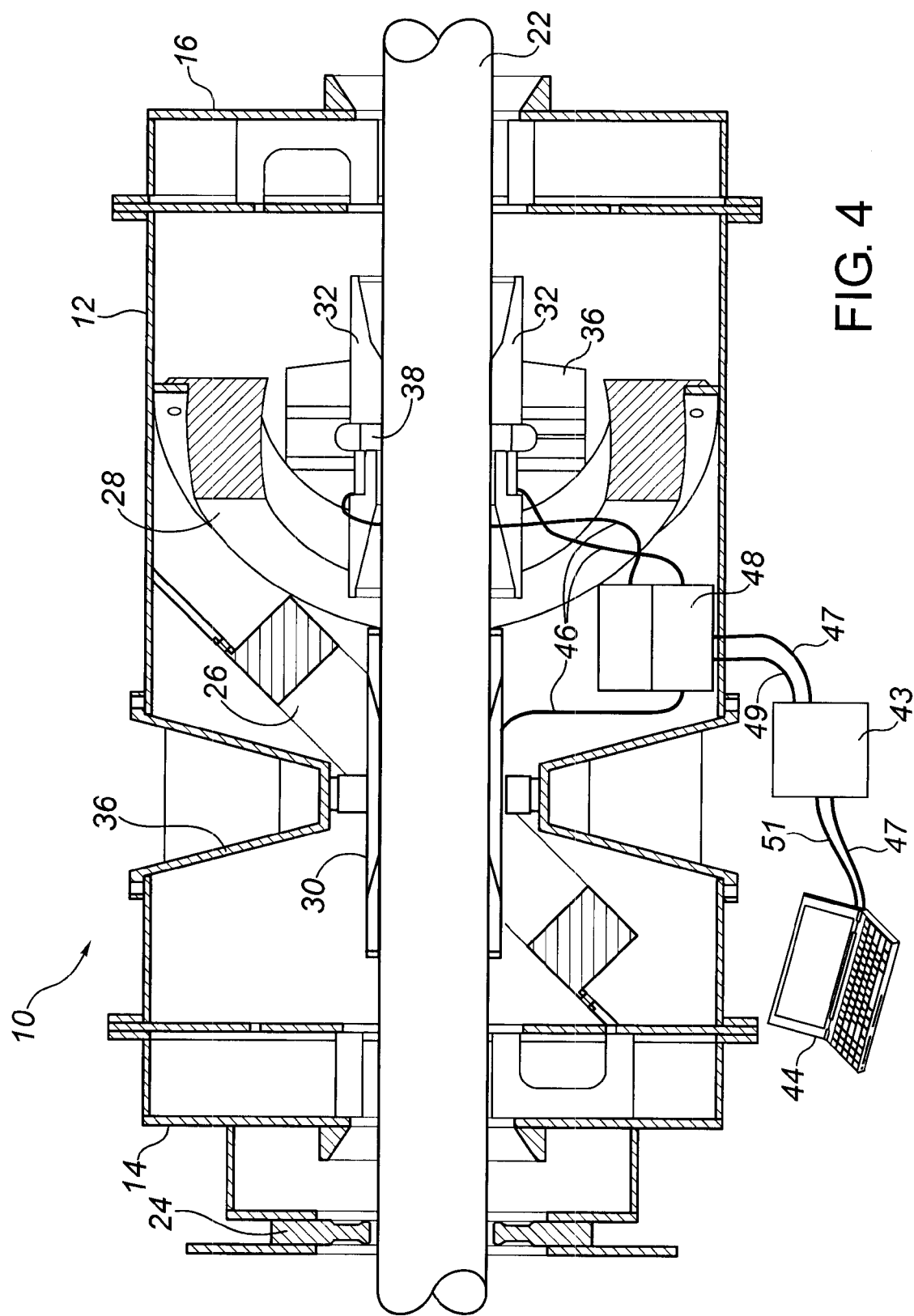
FIG. 4 is a front elevation view, in section, of the apparatus illustrated in FIG. 1, as a conduit passes through the conduit travel passage.

As illustrated in FIGS. 1 and 4, first pair of sensor supports 30, second pair of sensor supports 32 and sensor arrays 38 are positioned so as to provide flux pattern detection over the 360 degree circumference. A computer 44 is connected by cables 46 to communicate with sensor arrays 38 of each of first pair of sensor supports 30 and second pair of sensor supports 32. Computer 44 is adapted to receive and interpret signals from sensor arrays 38 of each of first pair of sensor supports 30 and second pair of sensor supports 32. In order to facilitate the transfer of signal data, a data processing board called a "hub box" 48 is incorporated in apparatus 10. Hub box 48 is used to communicate digital signals from sensor arrays 38 to computer 44.

Referring to FIG. 10, each of first pair of sensor supports 30 and second pair of sensor supports 32 are pivotally mounted for limited pivotal movement about a centrally positioned transverse axis 50.

Figure 11:
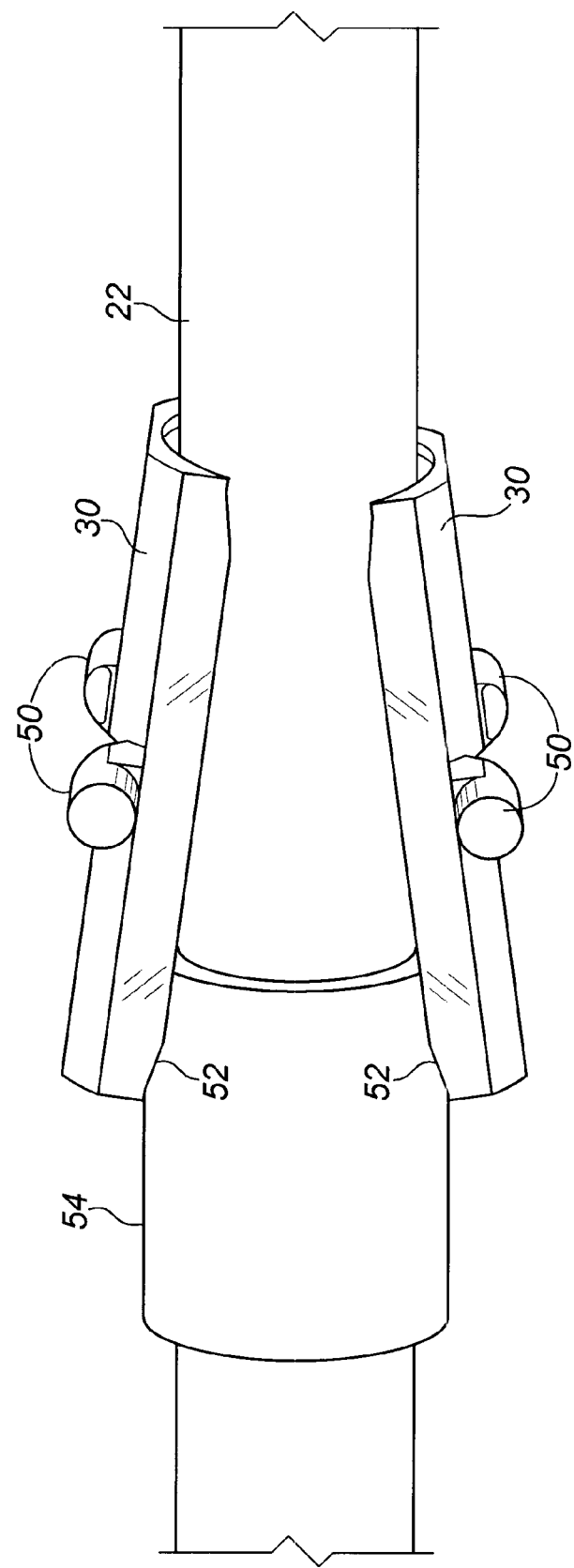
FIG. 11 is a side elevation view of the sensor supports as a conduit with a joint begins to pass between the sensor supports of the apparatus illustrated in FIG. 9.

As shown in FIG. 11, each of first pair of sensor supports 30 and second pair of sensor supports 32 have a wedge shaped inclined interior contact surface 52 on at least one end.

Figure 12:
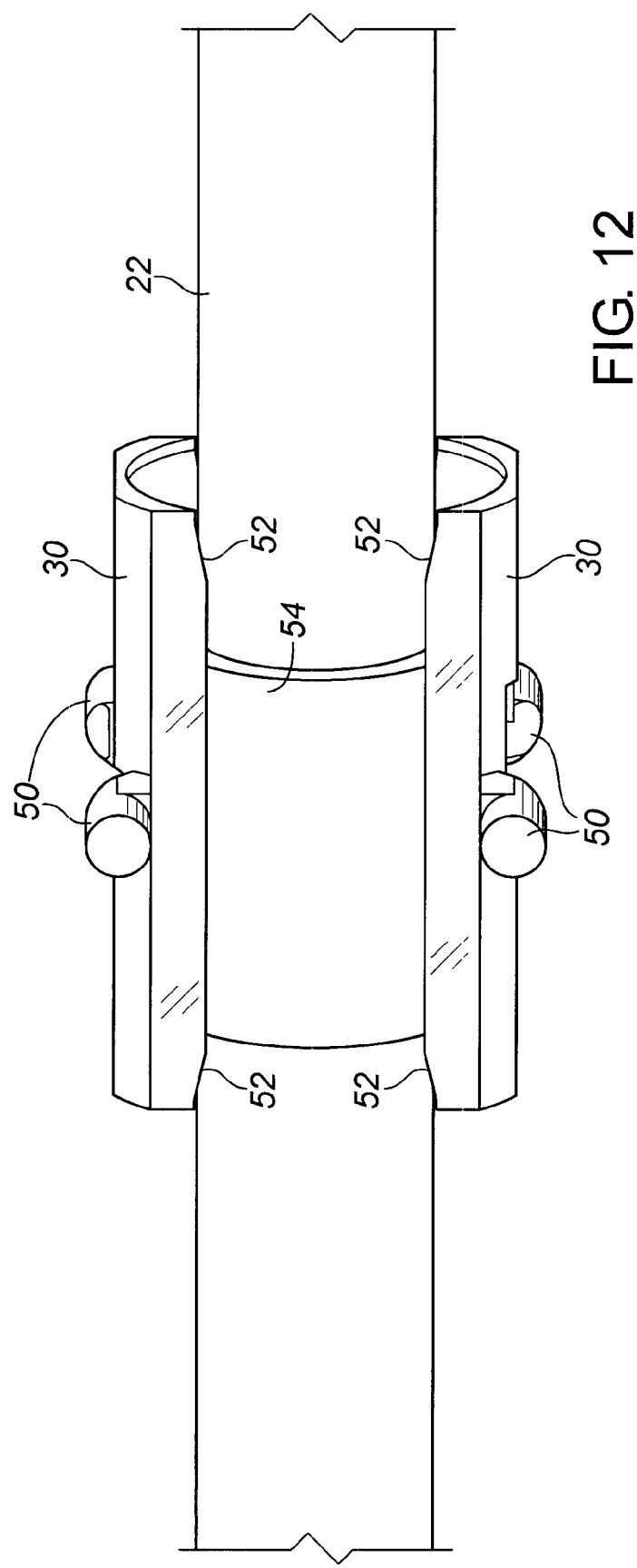
FIG. 12 is a side elevation view of the sensor supports as a conduit with a joint passes between the sensor supports of the apparatus illustrated in FIG. 9.
Figure 13:
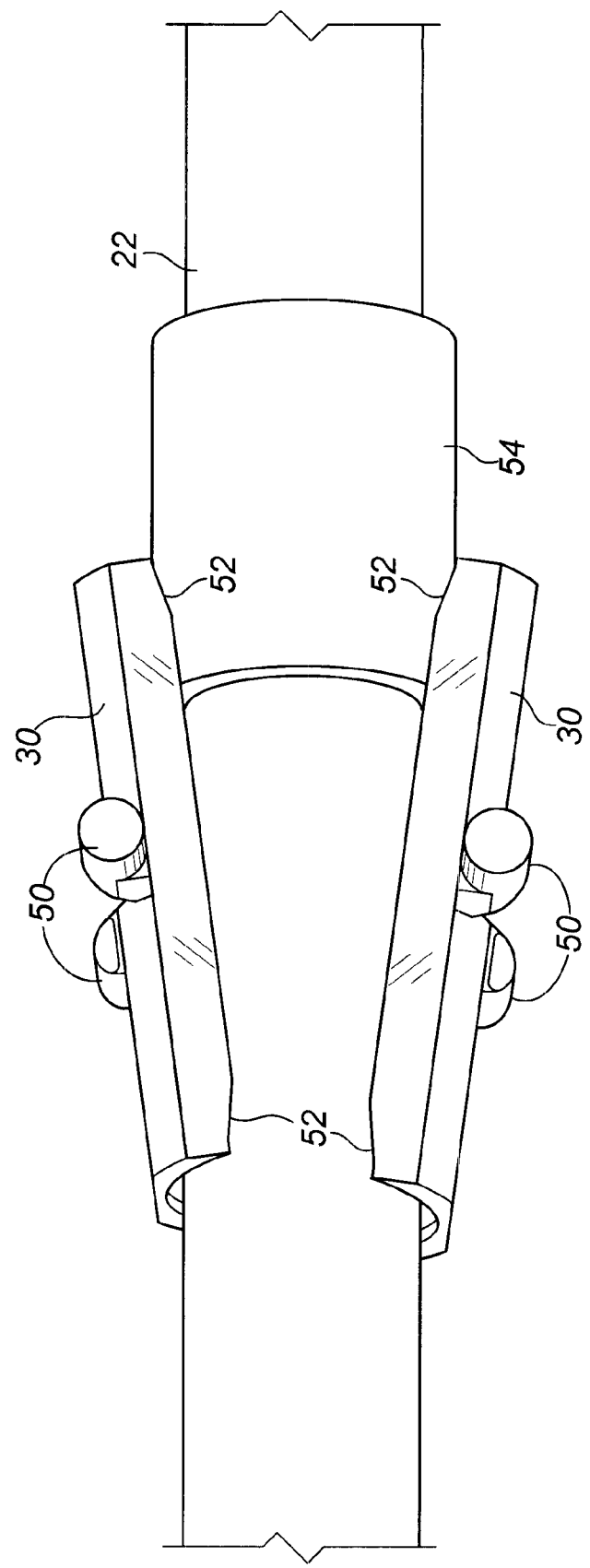
FIG. 13 is a side elevation view of the sensor supports as a conduit with a joint exits from between the sensor supports of the apparatus illustrated in FIG. 9.

By mounting each of first pair of sensor supports 30 and second pair of sensor supports 32 on springs 34 as illustrated in FIG. 6, the spacing between each first pair of sensor supports 30 and each of second pair of sensor supports 32 adjusts when passing over joints 54 in conduit 22 as illustrated in FIGS. 11 through 13.

EXAMPLE

In construction of proto-type apparatus, the coils used had 959 turns of 14 gauge copper wire. This coil was operated at Already current of 5.0 amps for inspection of 3.5 inch conduit. This combination was found to allow the apparatus to be used safely without excessive heat that could damage internal electronics. Although it proved appropriate for the inspection of 3.5 inch conduit, the number of turns, gauge of wire and current may not be optimum for conduit of other sizes. Each concave sensor support had two sensor boards of 18 sensors arranged in an arcuate pattern. One of the sensor boards serves to detect flux that is present radially in relation to the conduit travel passage in the same direction as the conduit. This flux is used to identify circumferential wear patterns. The other of the sensor board serves to detect flux that is present transverse to the conduit travel path across the conduit. This flux is used to detect the presence of longitudinal wear patterns. Two coils were used oriented at 45 degrees and offset by 90 degrees to produce 90 degree flux on opposing sides of the conduit. In combination the two coils. produced flux over the entire 360 degree circumference of the conduit. The signals from the sensors were sent across 50 meters of cable and captured by the computer. This data was compared to baseline data collected from new, non-worn conduit, the difference being an indication of the degree of wear. A high volume of data was found to be necessary in order to measure very small differences in flux. In order to facilitate the transfer of data a data processing board called a "hub box" was incorporated in the apparatus and used to transmit digital signals to the computer. A conduit without any wear produced a flux pattern shaped similarly to that illustrated in FIG. 15. This flux pattern can be graphically represented as follows:

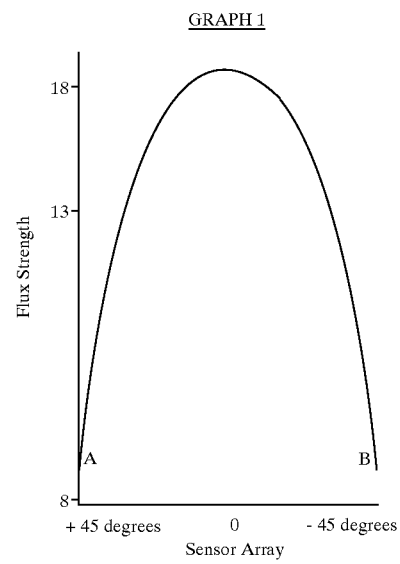

Figure 16:
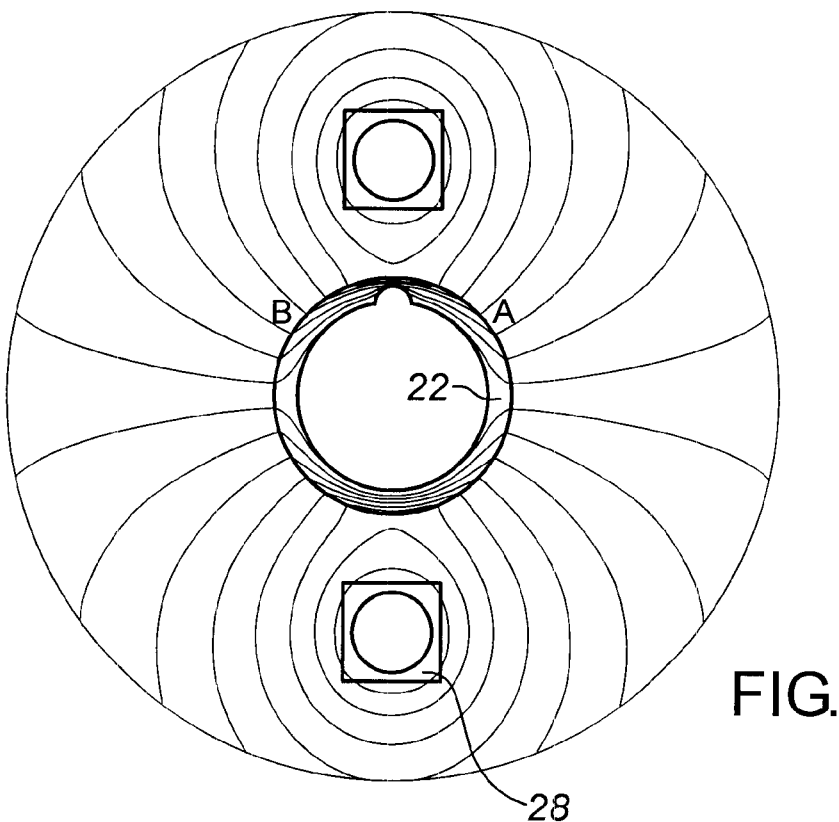
FIG. 16 is an end elevation view of a flux pattern in a conduit with a defect in a first position, as detected by the apparatus illustrated in FIG. 1.

When longitudinal wear was present on the inside of the conduit, a flux pattern was produced as illustrated in FIG. 16. This flux pattern can be graphically represented as set forth below:

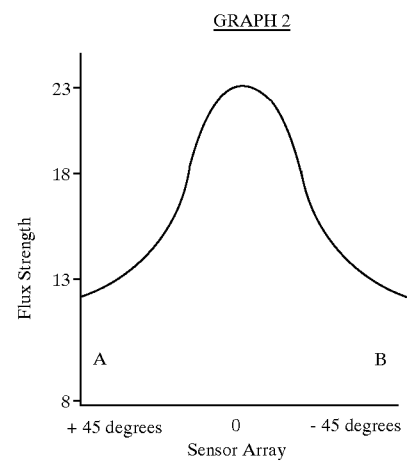

Figure 17:
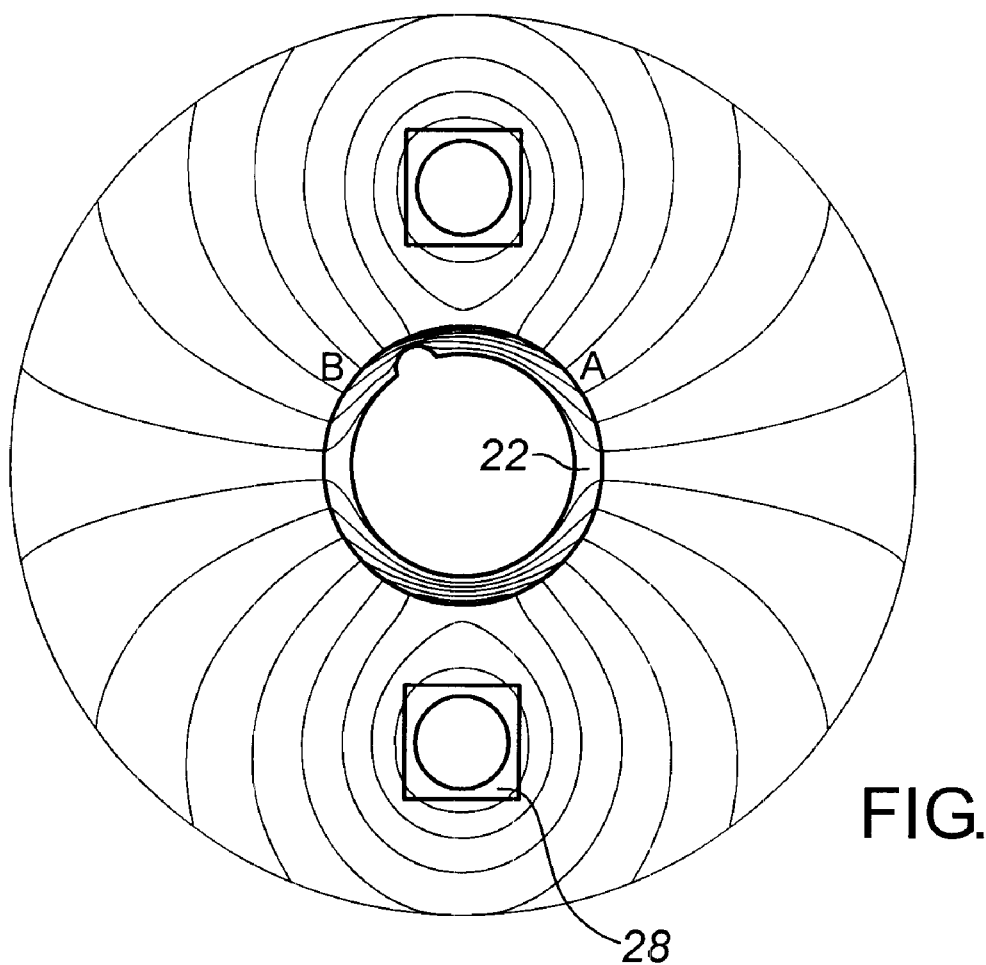
FIG. 17 is an end elevation view of a flux pattern in a conduit with a defect in a second position, as detected by the apparatus illustrated in FIG. 1.

The distribution of the flux density changes as the location of the wear in the conduit changes relative to the sensor supports, as illustrated in FIG. 17. This shift in the flux pattern can be graphically represented as set forth below:

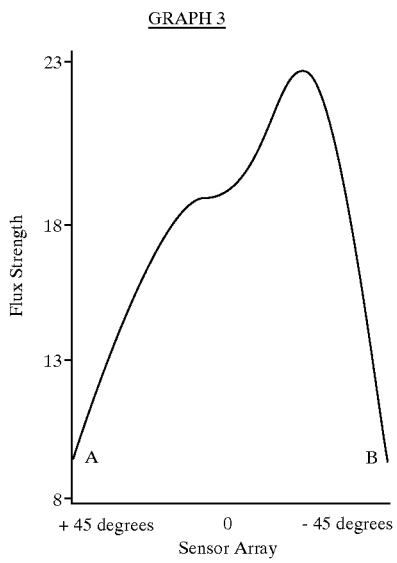

GRAPH 3

Operation:

The use and operation of apparatus 10 will now be described with reference to FIGS. 1 through 17.

Figure 14:
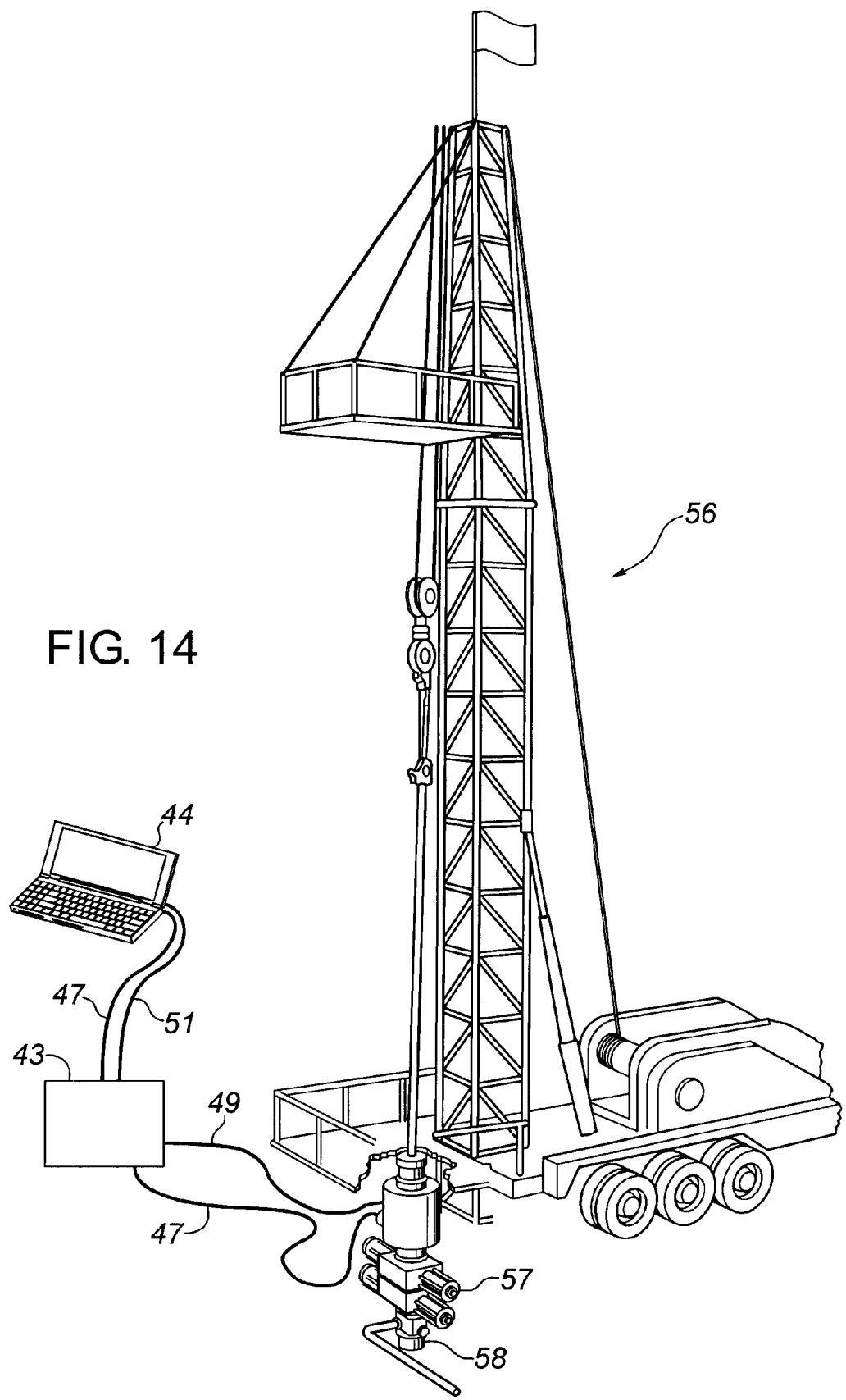
FIG. 14 is a perspective view of the apparatus illustrated In FIG. 1, in a field conduit inspection application.

Referring to FIGS. 1 and 14, apparatus 10 is transported to a well 56 located on a well site when inspection of conduit 22 for potential wear patterns is desired. Well 56 has a blow out preventer 57 and well head 58 through which conduit 22 is inserted and withdrawn. Apparatus 10 is secured to blow out preventer 57 located above well head 58, so that all conduit 22 inserted or withdrawn through blow out preventer 57 and wellhead 58 must pass through conduit travel passage 18 of apparatus 10.

The computer 44 is connected to the hub box 48 using cables 47 as illustrated in FIG. 4. Power is then provided toy first coil 26 and second coil 28 as well as to hub box 48 and sensor arrays 38 using cable 49. Computer 44 is activated and data collection software is loaded so that computer 44 is ready to begin receiving data. Referring to FIG. 14, power control box 43 is provided which enables computer 44 to using cable 51, to control amperage and maintain amperage as constant as possible. Data flows through power control box 43 but data is not manipulated by power control box 43. it will be appreciated that while power control box 43 is illustrated as resting on the ground, power control box 43 is generally truck mounted.

Conduit 22 is pulled through conduit travel passage 18 illustrated in FIG. 4. Resilient annular wiper 24 engages conduit 22 thereby removing excess oil which may cling to conduit 22.

Figure 2:
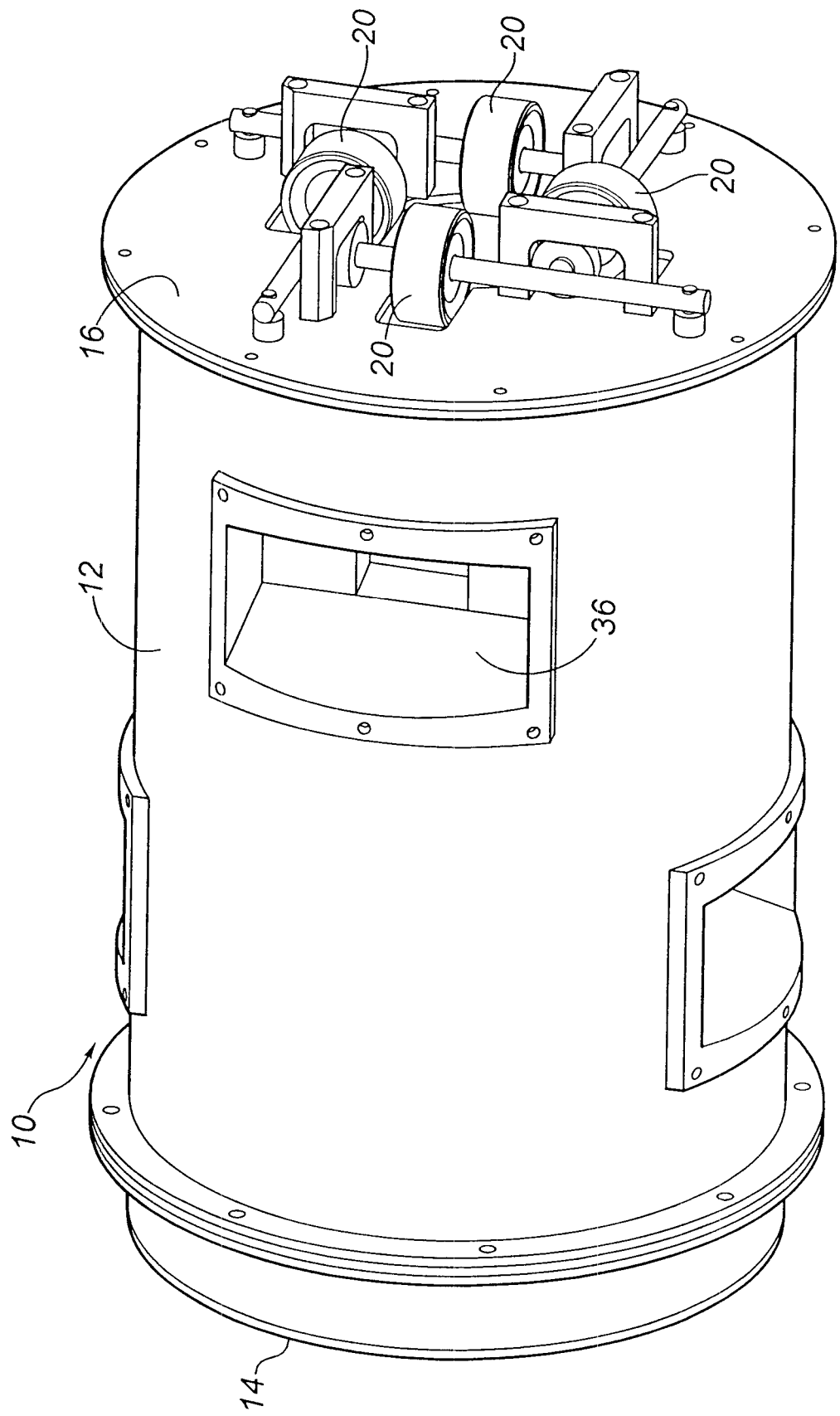
FIG. 2 is a perspective view of the apparatus illustrated in FIG. 1.
Figure 5:
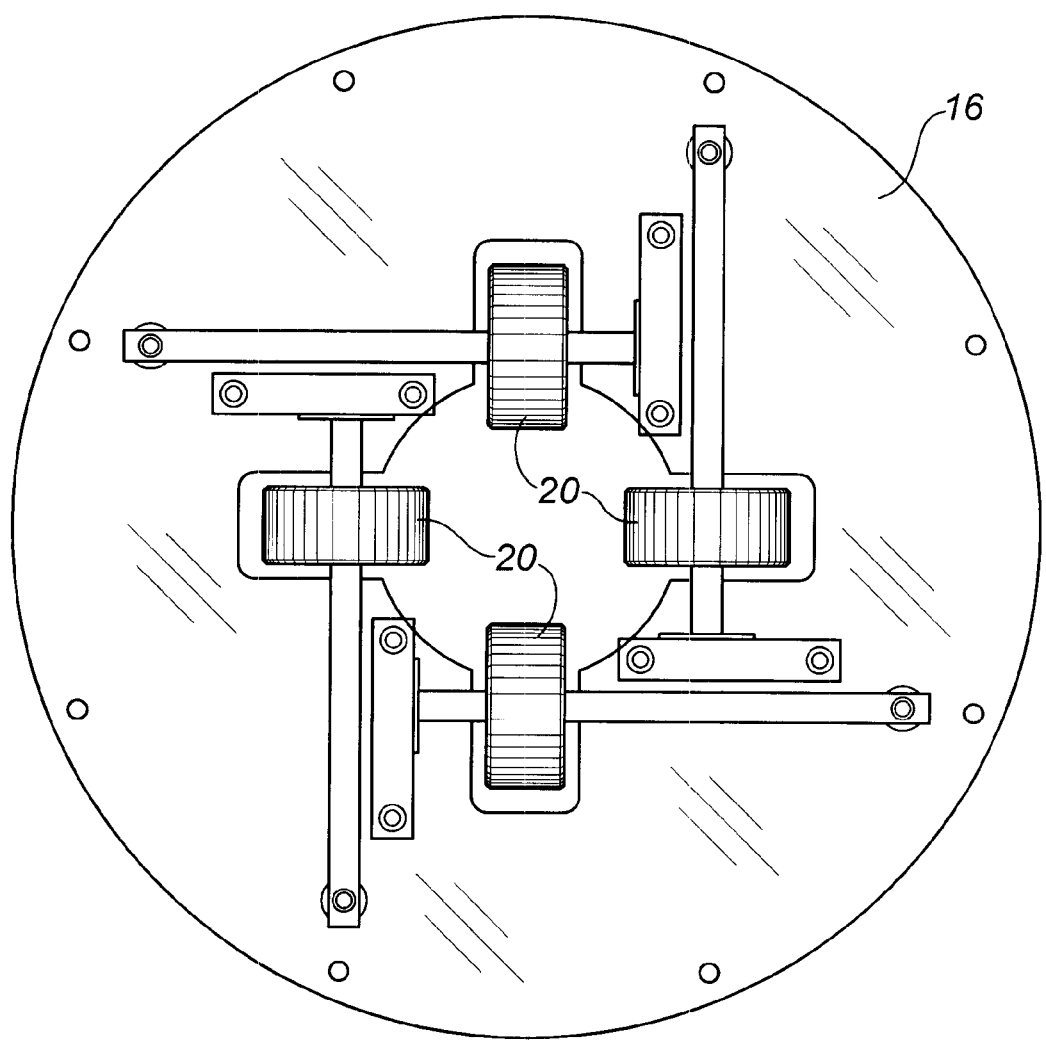
FIG. 5 is a bottom plan view of the apparatus illustrated in FIG. 1.

As illustrated in FIGS. 2 and 5, spring biased guide rollers 20 mounted to housing 12 operate to center housing 12 around conduit 22 as conduit 22 passes into and through conduit travel passage 18. It is important that conduit is properly centered as conduit 22 passes through conduit travel passage 18 to ensure accurate data results. Spring biased rollers 20 can move outwardly so as to accommodate the wider circumference of joints 54 along conduit 22 as conduit 22 continually moves into and through conduit travel passage 18.

Referring to FIG. 4, as conduit 22 passes through first pair of sensor supports 30, conduit 22 is also passing through first coil 26. As conduit 22 passes through first pair of sensor supports 30 with sensory arrays 38 and first coil 26, flux is detected and converted to digital signals that are collected and forwarded by hub box 48 to computer 44.

When joint 54 of conduit 22 is moved through first pair of sensor supports 30 as illustrated in FIG. 10, wedge shaped inclined contact surfaces 52 of first pair of sensor supports 30 glide up onto joint 54 and cause first pair of sensor supports 30 to pivot on centrally positioned transverse axis 50 as illustrated in FIG. 11. Furthermore, springs 34 on which first pair of sensor supports 30 are mounted permit first pair of sensor supports 30 to move outward so as to allow for the larger circumference of joint 54 to pass between them. When joint 54 is positioned fully between first pair of sensor supports 30, first pair of sensor supports 30 will be parallel to joint 54 as illustrated in FIG. 12.

As illustrated in FIG. 9, the concave shape of first pair of sensor supports 30 creates a gap between passing joint 54 and first pair of sensor arrays 38 so as to minimize the possibility of damage to sensor arrays 38 mounted on first pair of sensor supports 30. As joint 54 of conduit 22 passes beyond first pair of sensor supports 30, sensor supports 30 again pivots on centrally positioned transverse axis 50 so as to permit first pair of sensor supports 30 to again conform closely to conduit 22 as illustrated in FIG. 13.

After passing into and through first pair of sensor supports 30, conduit 22 proceeds to move through conduit travel passage 18 and into and through second pair of sensor supports 32. As conduit 22 passes through second pair of sensor supports 32, conduit 22 also passes through second coil 28 and sensor arrays 38 mounted on second pair of sensor supports 32. As with first pair of sensor arrays 38, flux is detected, converted to digital signals and sent by hub box 48 to computer 44 as illustrated in FIG. 4.

Second pair of sensor supports 32 engage joints 54 in conduit 22 in the same manner as first pair of sensor supports 30 as described above.

As illustrated in FIG. 3, first coil 26 and second coil 28 are oriented at 45 degrees and offset by 90 degrees to produce two flux components at 45 degrees to the direction of travel of conduit 22 through conduit travel passage 18. In combination first coil 26 and second coil 28 produce flux over the entire 360 degree circumference of conduit 22. First pair of sensor supports 30 and second pair of sensor supports 32 are positioned within housing 12 so as to provide flux pattern detection over a 360 degree circumference.

As illustrated in FIGS. 7 and 8, first sensor array 40 of each of sensor arrays 38 is oriented so as to detect flux which extend radially relative to conduit travel passage 18. This flux is used to identify circumferential wear patterns. Second sensor array 42 is oriented so as to detect flux which extend transversely relative to conduit travel passage 18. This flux is used to detect the presence of longitudinal wear patterns.

Figure 15:
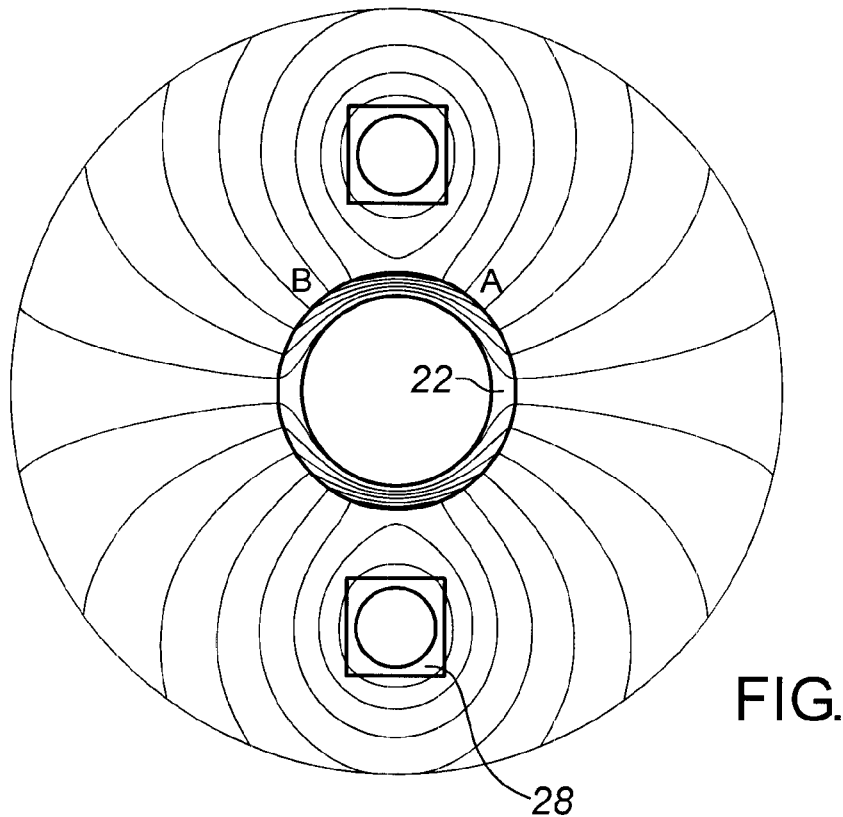
FIG. 15 is an end elevation view of a flux pattern in a conduit without defects, as detected by the apparatus illustrated in FIG. 1.

Data collected from this arrangement are analyzed by computer software installed on computer 44 which displays the resulting flux patterns in the form of graphs. An operator may then view and interpret the graphs for indicators of wear patterns in conduit 22. Conduit 22, first coil 28, along with various flux patterns are shown in FIGS. 15, 16 and 17. A conduit 22 without any wear produces a flux pattern as illustrated in FIG. 15 and GRAPH 1. This flux pattern represents the baseline data from new non-worn conduits which is used to compare against flux pattern obtained from used conduits 22. Any differences observed between the baseline flux pattern and flux patterns obtained from analyzing used conduits 22 indicate wear patterns which can make conduit 22 prone to rupture. As an example, if longitudinal wear is present on the inside of conduit 22, a flux pattern is produced as illustrated in FIG. 16 and GRAPH 2. The distribution of the flux density changes as the location of the wear inside of conduit changes relative to the sensor arrays, as illustrated in FIG. 17 and GRAPH 3. Although coil 28 is shown in FIGS. 15, 16 and 17, coil 26 would generate the same graphs.

It has been determined that the sensitivity of the apparatus to small imperfections can be enhanced when the amperage in the coil is kept constant. It has been determined that the large volume of data generated can best be handled when analog signals from the sensors are immediately converted to digital signals at their source prior to communication to the computer.

Variations and Alternative Embodiments:

Although apparatus 10 has been illustrated with two coils, once the teachings of the present invention are understood apparatus 10 can be made to work with a single coil or with more than two coils. There is no need for the angle of the coils to be 45 degrees, 45 degrees merely happens to be the best configuration for a two coil version of the invention. It is also possible to build a single coil in a FIG. 8 or some similar configuration, that can have the same effect as multiple coils.

Although apparatus 10 is shown in a stationary orientation with conduit being passed through it, it will be appreciated that all that is necessary is for there to be relative movement of the conduit and the conduit travel passage of the apparatus. Conduit can be inspected while sitting on storage racks. The conduit can remain stationary while the housing moves, the housing can remain stationary while the conduit moves, or the conduit and the housing can move relative to one another.

Cautionary Warnings:

The more turns of wire in the coils, the stronger the the field strength tends to be. The size of wire has an effect on the number of turns that can fit into the coil. A smaller gauge of wire permits more turns in the coil, but increases the potential for heat build-up. The objective should be for strongest field strength possible without creating an undesirable heat build-up.

It has been found of critical importance to maintain amperage as constant as possible. Where the amperage varies, small abnormalities remain undetected. In copper wire, five amps has been found to be ideal. When the amperage was increased beyond five amps, there was a dramatic increase in heat build-up which was viewed as being undesirable. If alternative materials were used, it may be that a different amperage threshold could be reached before heat build up became a factor.

In order to make the system work the frequency of data capture must be far greater than that which is required for circumferential wear detection. The prior art systems were using an averaging approach which is unacceptable for the degree of resolution longitudinal wear pattern detection requires. In order to provide an indication of the magnitude of conduit wear, the proto-type system operates with approximately 500 readings per second.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. An apparatus for the magnetic inspection of ferrous conduit for signs of wear, comprising:
    a housing having a first end, a second end and a conduit travel passage extending through the housing from the first end to the second end;
    at least two coils positioned within the housing and encircling the conduit travel passage, each of the at least two coils being disposed at a different angle to the conduit travel passage so as to create at least two transverse flux components;
    sensor supports positioned along the conduit travel passage and encircled by the at least two coils;
    at least one sensor array mounted on each of the sensor supports, the at least one sensor array being oriented to detect flux patterns which extend transversely relative to the conduit travel passage; and
    a computer in communication with the at least one sensor array, the computer being adapted to receive and interpret signals from the at least one sensor array.

2. The apparatus as defined in claim 1, wherein the sensor supports and at least one sensor array are positioned to provide flux pattern detection over a 360 degree circumference.

3. The apparatus as defined in claim 1, wherein a first sensor array is mounted on the sensor supports, the first sensor array being oriented to detect flux patterns which extend radially in relation to the conduit travel passage; and
    a second sensor array is mounted on the sensor supports, the second sensor array being oriented to detect flux patterns which extend transversely relative to the conduit travel passage.

4. The apparatus as defined in claim 1, wherein:
    a first coil is positioned within the housing encircling the conduit travel passage at a first angle;
    a second coil is positioned within the housing encircling the conduit travel passage at a second angle;
    a first pair of sensor supports is positioned in parallel spaced relation on opposed sides of the conduit travel passage within the first coil; and
    a second pair of sensor supports is positioned in parallel spaced relation on opposed sides of the conduit travel passage within the second coil, the second pair of sensor supports being offset by 90 degrees from the first pair of sensor supports.

5. The apparatus as defined in claim 1, wherein the sensor supports are concave and are oriented to conform to the contour of conduit passing through the conduit travel passage.

6. The apparatus as defined in claim 1, wherein the sensor supports are mounted on springs, thereby enabling spacing between the sensor supports to adjust when passing over joints in conduit.

7. The apparatus as defined in claim 1, wherein the sensor supports are mounted for limited pivotal movement about a centrally positioned transverse axis.

8. The apparatus as defined in claim 7, wherein the sensor supports have a wedge shaped inclined interior contact surface on at least one end.

9. The apparatus as defined in claim 1, wherein spring biased guide rollers are mounted to the housing surrounding the conduit travel passage to center housing around conduit passing through the conduit travel passage.

10. The apparatus as defined in claim 1, wherein a resilient annular wiper encircles the conduit travel passage and engages conduit prior to passing through the conduit travel passage to remove excess oil.

11. An apparatus for the magnetic inspection of ferrous conduit for signs of wear, comprising:
- a housing having a first end, a second end and a conduit travel passage extending through the housing from the first end to the second end;
- a first coil positioned within the housing encircling the conduit travel passage, the first coil being disposed at a first angle of approximately 45 degrees to the conduit travel passage so as to create a transverse flux component;
- a second coil positioned within the housing encircling the conduit travel passage, the second coil being disposed at a second angle of approximately 45 degrees to the conduit travel passage so as to create a transverse flux component perpendicular to that produced by the first coil;
- a first pair of sensor supports positioned in parallel spaced relation on opposed sides of the conduit travel passage within the first coil, the first pair of sensor supports being concave and oriented to conform to the contour of conduit passing through the conduit travel passage;
- a second pair of sensor supports positioned in parallel spaced relation on opposed sides of the conduit travel passage within the second coil, the second pair of sensor supports being offset by 90 degrees from the first pair of sensor supports, the second pair of sensor supports being concave and oriented to conform to the contour of conduit passing through the conduit travel passage;
- sensor arrays mounted on each of the first pair of sensor supports and the second pair of sensor supports, including:
  - a first sensor array oriented to detect flux patterns which extend radially relative to the conduit travel passage, and
  - a second sensor array oriented to detect flux patterns which extend transversely relative to the conduit travel passage;
- the first pair of sensor supports, the second pair of sensor supports and sensor arrays being positioned to provide flux pattern detection over a 360 degree circumference; and
- a computer in communication with the sensor arrays of each of the first pair of sensor supports and the second pair of sensor supports, the computer being adapted to receive and interpret signals from the sensor arrays of each of the first pair of sensor supports and the second pair of sensor supports.

12. The apparatus as defined in claim 11, wherein each of the first pair of sensor supports and the second pair of sensor supports are mounted for limited pivotal movement about a centrally positioned transverse axis.

13. The apparatus as defined in claim 11, wherein each of the first pair of sensor supports and the second pair of sensor supports have a wedge shaped inclined interior contact surface on at least one end.

14. The apparatus as defined in claim 11, wherein each of the first pair of sensor supports and the second pair of sensor supports are mounted on springs, thereby enabling the spacing between the sensor supports to adjust when passing over joints in conduit.

15. The apparatus as defined in claim 11, wherein guide rollers are mounted to the housing surrounding the conduit b travel passage to center the housing around conduit passing through the conduit travel passage.

16. The apparatus as defined in claim 11, wherein a resilient annular wiper encircles the conduit travel passage and engages conduit prior to passing through the conduit travel passage to remove excess oil.

17. A method for the magnetic inspection of ferrous conduit for signs of wear, comprising the steps of:
- positioning at least two coils encircling a conduit travel path each at a different angle so as to create at least two transverse flux components;
- positioning a sensor array within each of the at least two coils, with each sensor array oriented to detect flux patterns which extend transversely relative to the conduit travel passage; and
- using a computer in communication with each sensor array to receive and interpret signals from each sensor array.

18. The method as defined in claim 17, amperage in the at least two coils being kept constant.

19. The method as defined in claim 17, analog signals from each sensor array being immediately converted to digital signals at their source prior to communication to the computer.

* * * * *

UNITED STATES PATENT AND TRADEMARK OFFICE
CERTIFICATE OF CORRECTION

PATENT NO. : 6,483,302 B1
DATED : November 19, 2002
INVENTOR(S) : D.G. Rusnell et al.

It is certified that error appears in the above-identified patent and that said Letters Patent is hereby corrected as shown below:

<u>Column 12,</u>
Line 22, "b travel" should read -- travel --

Signed and Sealed this

Twenty-fifth Day of March, 2003

JAMES E. ROGAN
*Director of the United States Patent and Trademark Office*